(12) United States Patent
Kondo et al.

(10) Patent No.: US 7,709,255 B2
(45) Date of Patent: May 4, 2010

(54) NERVE CELLS OBTAINED BY ELECTRIC PULSE TREATMENT OF ES CELLS

(75) Inventors: Takashi Kondo, Wako (JP); Masahisa Yamada, Wako (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 10/559,132

(22) PCT Filed: Jun. 2, 2004

(86) PCT No.: PCT/JP2004/007607

§ 371 (c)(1),
(2), (4) Date: Apr. 24, 2006

(87) PCT Pub. No.: WO2004/108907

PCT Pub. Date: Dec. 16, 2004

(65) Prior Publication Data

US 2007/0065941 A1 Mar. 22, 2007

(30) Foreign Application Priority Data

Jun. 3, 2003 (JP) ............................. 2003-158017

(51) Int. Cl.
*C12N 5/02* (2006.01)
*C12N 5/08* (2006.01)
*C12N 13/00* (2006.01)

(52) U.S. Cl. ...................... 435/368; 435/366; 435/377; 435/173.1

(58) Field of Classification Search ....................... None
See application file for complete search history.

(56) References Cited

U.S. PATENT DOCUMENTS

2004/0092012 A1 5/2004 Okano et al.

FOREIGN PATENT DOCUMENTS

| EP | 1302536 | 4/2003 |
| JP | 2002-291469 | 10/2002 |

OTHER PUBLICATIONS

Okano H. Neural stem cells: progression of basic research and perspective for clinical application. Keio Journal of Medicine 51(3): 115-128. Sep. 2002.*

Romero-Ramos et al, Journal of Neuroscience Research, 69:894-907, Sep. 15, 2002.*

Jain KK, Mol Biotechnol., Mar. 28, 2009.*

Reubinoff, BE et al., Nat. Biotechnol., Dec. 2001, vol. 19(12), pp. 1134-1140.

Zhang, S.C. et al., Nat.Biotechnol., Dec. 2001, vol. 19(12), pp. 1129-1133.

Brustle, O. et al., Science. Jul. 30, 1999, vol. 285 (5428), pp. 754-756.

Okabe, S. et al., Mech. Dev., Sep. 1996, vol. 59(1), pp. 89-102.

Sauer, H. et al., J. Cell. Biochem., Dec. 15, 1999, vol. 75(4), pp. 710-723.

Freeman, M. et al., "Regulatory principles of developmental signaling", Annu. Rev. Cell. Dev. Biol., 2002, vol. 18, pp. 515-539.

Coucouvanis, E. et al., "BMP signaling plays a role in viceral endoderm differentiation and cavitation in the early mouse embryo", Development, 1999, vol. 126. pp. 535-546.

Lee, S. H. et al., "Efficient generation of mid brain and hindbrain neurons from mouse embryonic stem cells", Nat. Biotechnol., 2000, vol. 18, pp. 675-679.

Lumelsky, N. et al., "Differentiation of embryonic stem cells to insulin-secreting structures similar to pancreatic islets", Science, 2001, vol. 292, pp. 1389-1394.

Wichterle, H. et al., "Directed differentiation of embryonic stem cells into motor neurons", Cell, 2002, vol. 110, pp. 385-397.

Johe, K. K. et al., "Single factors direct the differentiation of stem cells from the fetal and adult central nervous system", Genes. Dev., 1996, vol. 10, pp. 3129-3140.

Kawasaki, H. et al., "Induction of midbrain dopaminergic neurons from ES cells by stromal cell-derived inducing activity", Neuron, 2000, vol. 28, pp. 31-40.

Zhang, L. I. et al., "Electrica activity and development of neuronal circuits", Nat. Neurosci., 2001, vol. 4, pp. 1207-1214.

Nagai, T. et al., "A variant of yellow flurescent protein with fast and efficient maturation for cell-biological applications", Nat. Biotechnol., 2002, vol. 20, pp. 87-90.

(Continued)

*Primary Examiner*—John D. Ulm
*Assistant Examiner*—Stacey MacFarlane
(74) *Attorney, Agent, or Firm*—Birch, Stewart, Kolasch & Birch, LLP

(57) ABSTRACT

It is an object of the present invention to apply a novel method of preparing neural cells from ES cells. The method of the present invention is characterized by the electric pulse treatment of differentiating ES cells. Nerve cells obtained by the method of the present invention have the flexibility to differentiate into a variety of types of neurons in vivo preferably without the need for application of growth factors.

7 Claims, 7 Drawing Sheets

OTHER PUBLICATIONS

Tanabe, Y. et al., "Specification of motor neuron identity by MNR2 homeodomain protein", Cell, 1998, vol. 95, pp. 67-80.

Wu, P. et al., "Region-specific generation of cholinergic neurons from fetal human neural stem cells grafted in adult rat", Nat. Neurosci., 2002, vol. 5, pp. 1271-1278.

Tsuchida, T. et al., "Topographic organization of embryonic motor neurons defined by expression of LIM homeobox genes", Cell, 1994, vol. 79, pp. 957-970.

Rubio, F. J. et al., "Genetically perpetuated human neural stem cells engraft and differentiate into the adult mammalian brain", Mol. Cell. Neurosci., 2000, vol. 16, pp. 1-13.

Beattie, M. S. et al., "Endogenous repair after spinal cord contusion injuries in the rat", Exp. Neurol., 1997, vol. 148, pp. 453-463.

Cassidy, R. et al., "Neurobiology: Stem cells on the brain", Nature, 2001, vol. 412, pp. 690-691.

Kim, J. H. et al., "Dopamine neurons derived from embryonic stem cells function in an animal model of Parkinson's disease", Nature, 2002, vol. 418, pp. 50-56.

Janicak, P. G. et al., "Efficacy of ECT: a meta-analysis", Am. J. Phychiatry, 1985, vol. 142, pp. 297-302.

Niwa, H. et al., "Efficient selection for high-expression transfectants with a novel eukaryotic vector", Gene, 1991, vol. 108, pp. 193-199.

Martin, Proc. Natl. Acad. Sci., USA, 1981, vol. 78, pp. 7634-7638.

Evans, Nature, 1981, vol. 292, pp. 154-156.

Iannaconns et al., Dev. Biol., 1994, vol. 163, pp. 288-292.

Doetschman et al., Dev. Biol., 1988, vol. 127, pp. 224-227.

Wheeler, Reprod. Fertil. Dev., 1994, vol. 6, pp. 563-568.

First et al., Reprod. Fertil. Dev., 1994, vol. 6, pp. 553-562.

Thompson et al., Proc. Natl. Acad. Sci., USA, 1995, vol. 92, pp. 7844-7848.

Thompson et al., Science, 1988, vol. 282, pp. 1145-1147.

Schamblott et al., Proc. Natl. Acad. Sci., USA, 1998, vol. 95, pp. 13726-13731.

Reubinoff, B. E. et al., Nature Biotech., 2000, vol. 18, pp. 399-404.

Campbell et al., Nature, 1996, vol. 380, pp. 64-66.

Tada, M. et al., Cur. Biol., 2001, vol. 11, pp. 1553-1558.

\* cited by examiner

NERVE CELLS OBTAINED BY ELECTRIC PULSE TREATMENT OF ES CELLS

This Application is the National Phase Under 35 U.S.C. §371 of PCT International Application No. PCT/JP2004/007607 which has an International filing date of Jun. 2, 2004, which claims priority to Japanese Application No. 2003-158017 filed on Jun. 3, 2003.

TECHNICAL FIELD

The present invention relates to neural cells obtained by electric pulse treatment of ES cells, to a method of preparing the neural cells and to an application therefore.

BACKGROUND ART

Cells and Differentiation

During the process of differentiation, tissue formation with harmonious differentiation and cell pattern formation is considered necessary for building the original construct that transmits the appropriate functions of the organs and ultimately for building the animal body. Interactions among individual cells and the environment surrounding them (which would generally consist of cells) are vital for assembling a complex and functional structure and for indicating to the cells how they should participate.

During the course of development, cells continuously receive various types of environmental signals for differentiation and pattern development. These two processes cannot be isolated, and no functional organ has yet been reconstructed in an ex vivo culture system. Although cell pattern formation is difficult to recreate in a culture system, many developmental signals related to differentiation have been studied in principle ex vivo. Many reagents have already been isolated as signals for differentiation, including cell-cell interactions and growth factors for example (Non-Patent Publication No. 1). These signals activate intercellular signaling pathways, causing a series of necessary reactions that ultimately cause transcriptional modifications, producing functional and finally differentiated cells. For all reactions to be achieved, the cells need to be exposed to these signals in a suitable order during the differentiation time frame.

The cerebral nervous system is constructed of neural cells with a variety of individual properties. Various neural-inducing factors have been identified in recent years from research in the fields of molecular genetics and molecular developmental biology, and the molecular mechanisms of early neural development from the undifferentiated ectoderm through nerve tissue are being elucidated. However, much is still unknown about the molecular mechanisms of early neural development in mammals and the mechanisms by which a variety of individual properties of mature neurons are determined. There is a demand for a model of the differentiation system capable of reproducing the neural development of mammals in particular either in vitro or in vivo.

Embryonic Stem Cells (ES Cells)

Pluripotent stem cells are stem cells present in the early stage of development that have pluripotency or in other words the ability to differentiate into all the tissue cells which make up an individual. For example, the fetus is built from cells derived from the inner cells mass of the blastocyst, the epiblast and the like, which are typical pluripotent stem cells. However, in the course of development the pluripotent stem cells separate into the cell lineages of three different germ layers, i.e., the ectoderm, mesoderm and endoderm, and are thought to have disappeared by the time the organs start to form. Consequently, they are not responsible for proliferation and self-replication during the life of an individual, and are different from tissue stem cells, which supply new cells to maintain the individual.

An embryonic stem cell (ES cell) line is a cell line which has been produced by recovering pluripotent stem cells present only for a short time during the early stage of development as described above and making into a cell line which can be cultured in vitro. Like pluripotent stem cells in the early embryo, ES cells are capable of effectively unlimited growth while maintaining the ability to differentiate into all the cells that make up an individual. It is expected that if methods can be established of inducing differentiation of ES cells into necessary functional cells, it will be possible to supply those functional cells needed for therapy. An ES cell line was first established from a mouse ICM in 1981 (Martin, Proc. Natl. Acad. Sci. USA 78: p. 7634-7638, 1981; Evans & Kaufman, Nature 292: p. 154-156, 1981). Since 1998, several research teams have succeeded in establishing human ES cell lines from human blastocyts (Thomson, J. A. et al., Science, 282, p. 1145, 1998; Shamblott et al., Proc. Natl. Acad. Sci. USA 95: 13726-13731, 1998; Rubinoff, B. E. et al., Nature Biotech 18, p. 399-404, 2000). These ES cell lines were established by culturing ICMs isolated from blastocysts on feeder cells.

Thus, ES cells are totipotent cells that differentiate with a variety of fates in vivo and ex vivo. When ES cells are cultured to high densities without the addition of a differentiation-inhibiting factor such as LIF (leukemia inhibitory factor), or are formed into a cell mass by a float culture with adhesion to the culture dish prevented, they naturally differentiate into a variety of cells. In particular, a cell mass formed by float culture is called an embryoid body (EB), and is the most widely used for differentiating ES cells in vitro. An embryoid body has a ball-like structure consisting of two cell layers, with the inner layer corresponding to the proximal endoderm and the outer layer to the embryonic ectoderm. These two layers are separated by a basement membrane. Within the embryoid body a mesoderm is induced, and muscle cells, blood vessel cells and even primitive vasoganglia develop. When the embryoid body is made to adhere to a culture dish and cultured still further, it differentiates into a variety of kinds of cells. These include neural cells, keratinocytes, cartilage cells, fat cells and the like. Cells differentiated after embryoid body formation are not necessarily somatic cells, and differentiation into a reproductive cell lineage has recently been confirmed.

Methods of inducing differentiation of ES cells in vitro also include methods involving secondary culture of ES cells on an extracellular matrix or a supporting layer of cells called stroma cells. Because it is easier to induce differentiation of different cell lineages from ES cells depending on the stroma cell line or extracellular matrix, this method is suited to selectively inducing differentiation into particular cell lineages.

Thus, after forming an embryoid body (EB) or the like ES cells can be induced to develop into a variety of forms, such as extraembryonic endoderm, neurons, muscle and the like (Non-Patent Publication No. 2). Many growth factors and signaling pathways have the ability to initiate the differentiate process and regulate the direction of cell differentiation (Non-Patent Publications No. 3-4). In the case of neural cells, several reports have already suggested that when various growth factors are applied, ES cells differentiate towards a number of specific neuron fates and contribute to certain parts that are fated to become neuron tissue (Non-Patent Publications No. 5-7). These individual growth factors have been shown to regulate differentiation ratios relatively efficiently.

However, much is still unknown about the molecular mechanisms of early neural development in mammals and the mechanisms by which a variety of individual properties of mature neural cells are determined. Currently known methods of regenerating neural cells from ES cells require the application of growth factors, and depending on the growth factors used ES cells differentiate into a variety of specific types of neural cells, including neurons, glia cells, astrocytes, oligodendrites and the like. Considering application to animals and clinical applications, there is a demand for means of preparing neural cells corresponding to neural stem cells with the flexibility to differentiate into a variety of types of neurons in vivo without requiring the application of growth factors.

Ion Balance or Electric Activity and Cell Differentiation

Ion balance or electric activity is one factor that cannot be negligible in homeostasis. Ions are known to have such biological functions as neurotransmission. The balance between intracellular and extracellular ion densities creates an electric potential, and cell conditions are maintained by a static ion balance. It is known that $Li^+$ and $Ca^{2+}$ concentrations affect differentiation fate by means of a phosphorylation cascade related to the Wnt-Frizzled pathway. Moreover, electric activity in differentiating neural circuits induces functional and structural improvement in many synapse connections, and activity-dependent gene transcription responses allow network activity to be more prominent (Non-Patent Publication No. 8). This suggests the importance of ion densities and electric activity for the differentiation process, but little has been reported about cell fate determination in connection with cellular and extracellular ion densities.

Non-Patent Publication 1: Freeman, M. & Gurgon, J. B. Regulatory principles of developmental signaling. Annu. Rev. Cell. Dev. Biol. 18, 515-539 (2002).

Non-Patent Publication 2: Coucouvanis, E. and Martin, G. R. BMP signaling plays a role in viceral endoderm differentiation and cavitation in the early mouse embryo. Development 126, 535-546 (1999).

Non-Patent Publication 3: Lee, S. H., Lumelsky, N., Studer, L., Auerbach, J. M. & McKay R. D. Efficient generation of mid brain and hindbrain neurons from mouse embryonic stem cells. Nat. Biothechnol. 18, 675-679 (2000)

Non-Patent Publication 4: Lumelsky, N., Blondel, O., Laeng, P., Velasco, I., Ravin, R. & McKay, R. Differentiation of embryonic stem cells to insulin-secreting structures similar to pancreatic islets. Science 292, 1389-1394 (2001).

Non-Patent Publication 5: Wichterle, H., Lieberam, I. Porter, J. A. and Jessell, T. M. Directed Differentiation of embryonic stem cells into motor neurons. Cell 110, 385-397 (2002).

Non-Patent Publication 6: Johe, K. K., Hazel, T. G., Muller, T., Duqich-Djordjevic, M. M. & Mckay R. D. Single factors direct the differentiation of stem cells from the fetal and adult central nervous system. Genes. Dev. 10, 3129-3140 (1996).

Non-Patent Publication 7: Kawasaki, H., Misuseki, K., Nishikawa, S., Kaneko, S., Kuwana, Y., Nakanishi, S., Nishikawa. S. & Sasai, Y. Induction of midbrain dopaminergic neurons from ES cells by stromal cell-derived inducing activity. Neuron 28, 31-40 (2000).

Non-Patent Publication 8: Zhang, L. I. & Poo, M. M. Electrica activity and development of neuronal circuits. Nat. Neurosci. 4 Suppl., 1207-1214 (2001).

Non-Patent Publication 9: Nagai, T., Ibata, K., Park, E. S., Kubota, M., Mikoshiba, K. & Miyawaki, A. A variant of yellow fluorescent protein with fast and efficient maturation for cell-biological applications. Nat Biotechnol. 20, 87-90 (2002).

Non-Patent Publication 10: Tanabe, Y., William, C. & Jessell, T. M. Specification of motor neuron identity by MNR2 homeodomain protein Cell 95, 67-80 (1998).

Non-Patent Publication 11: Wu, P., Tarasenko, Y. I., Gu, Y., Huang, L.-Y. M., Coggeshall, R. E. & Yu, Y. Region-specific generation of cholinergic neurons from fetal human neural stem cells grafted in adult rat. Nat. Neurosci. 5, 1271-1278 (2002).

Non-Patent Publication 12: Tsuchida, T., Ensini, M., Morton, S. B., Baldassare, M., Edlund, T., Jessell, T. M. & Pfaff, S. L. Topographic organization of embryonic motor neurons defined by expression of LIM homeobox genes. Cell 79, 957-970 (1994).

Non-Patent Publication 13: Rubio, F. J., Bueno, C., Villa, A., Navarro, B. & Martinez-Serrano, A. Genetically perpetuated human neural stem cells engraft and differentiate into the adult mammalian brain. Mol. Cell. Neurosci. 16, 1-13 (2000).

Non-Patent Publication 14: Beattie, M. S., Bresnahan, J. C., Komon, J., Tovar, C. A., Van Meter, M., Anderson, D. K., Faden, A. I., Hsu, C. Y., Noble, L. J., Salzman, S. & Young, W. Endogenous repair after spinal cord contusion injuries in the rat. Exp. Neurol. 148, 453-463 (1997).

Non-Patent Publication 15: Cassidy, R. & Frisen, J., Neurobiology: Stem cells on the brain. Nature 412, 690-691 (2001).

Non-Patent Publication 16: Kim, J. H., Auerbach, J. M., Rodriguez-Gomez, J. A., Velasco, I., Gavin, D., Lumelsky, N., Lee, S. H., Nguyen, J., Sanchez-Pernaute, R., Bankiewicz, K. & McKay, R. Dopamine neurons derived from embryonic stem cells function in an animal model of Parkinson's disease. Nature 418, 50-56 (2002).

Non-Patent Publication 17: Janicak, P. G., Davis, J. M., Gibbons, R. D., Ericksen, S., Chang, S. & Gallagher, P. Efficacy of ECT: a meta-analysis. Am. J. Psychiatry 142, 297-302 (1985).

Non-Patent Publication 18: Niwa, H., Yamamura, K. & Miyazaki, J. Efficient selection for high-expression transfectants with a novel eukaryotic vector. Gene 108, 193-199 (1991).

Non-Patent Publication 19: Martin, Proc. Natl. Acad. Sci. USA 78:p. 7634-7638, 1981

Non-Patent Publication 20: Evans & Kaufman, Nature 292:p. 154-156, 1981

Non-Patent Publication 21: Iannaconns et al., Dev. Biol. 163: p. 288-292, 1994

Non-Patent Publication 22: Doetschman et al., Dev. Biol. 127:p. 224-227, 1988

Non-Patent Publication 23: Wheeler, Reprod. Fertil. Dev. 6:p. 563-568, 1994

Non-Patent Publication 24: First et al., Reprod. Fertil. Dev. 6:p. 553-562

Non-Patent Publication 25: Thompson et al., Proc. Natl. Acad. Sci. USA 92:p. 7844-7848, 1995

Non-Patent Publication 26: Thompson et al., Science 282: 1145-1147, 1988

Non-Patent Publication 27: Shamblott et al., Proc. Natl. Acad. Sci. USA 95:13726-13731, 1998

Non-Patent Publication 28: Reubinoff, B. E. et al., Nature Biotech., 18, p. 399-404, 2000

Non-Patent Publication 29: Campbell et al., Nature 380:p. 64-66, 1996

Non-Patent Publication 30: Tada M. et al., Cur. Biol., 11:p. 1153-1158, 2001

DISCLOSURE OF THE INVENTION

Problems to be Solved by the Invention

It is an object of the present invention to provide a method of preparing neural cells in vitro or ex vivo. The method of the present invention comprises electric pulse treatment of differentiating ES cells.

In a preferred mode of the present invention, the electric pulse is applied at a power level in the range of 0.01 to 10 W or preferably 0.05 to 6 W.

In a preferred mode of the present invention, the differentiating ES cells are ES cells, differentiation of which has been induced by means of a float culture, stroma cells, extracellular matrix or a differentiation-inducing factor.

It is also an object of the present invention to provide neural cells prepared by the aforementioned method of the present invention. The neural cells of the present invention are non-reactive to exposure to growth factors in vitro or ex vivo, and/or are capable of final differentiation into specific neural cells in vivo.

It is also an object of the present invention to provide a pharmaceutical composition for preventing or diagnosing neural-related diseases or damage which comprises the neural cells of the present invention.

Means for Solving the Problems

The present inventors arrived at the present invention as a result of exhaustive research aimed at obtaining neural cells having the flexibility to differentiate into a variety of forms of neurons in vivo without requiring application of growth factors when they discovered that the ion density gradient and electric homeostasis are important for the differentiation process and in particular for regulating the fate determination of cells in the process of differentiation. ES cells that had begun to differentiate acquired a strong tendency to move towards differentiation into neuron cells when subjected to an electric pulse. The resulting neuron cells showed no signs of a specific final differentiation in an ex vivo culture line. That is, unlike ES cells which had been induced to differentiate into neurons with growth factors (Non-Patent Publications 5-7), they exhibited "destination flexibility" of cell type-specific determination, and exhibited the ability to form any neuron lineage in any tested neuron tissue. They also had the potential to differentiate into various types of neurons in vivo, indicating that they could contribute to animal bodies. The neural cells and preparation method therefore of the present invention offer not only the possibility of elucidating novel mechanisms in fundamental cell differentiation and neural development, but also the possibility of medical applications.

Method of Preparing Neural Cells

The method of preparing neural cells of the present invention is characterized by the treatment of differentiating ES cells with an electric pulse.

(1) ES Cells

In these specifications, "ES cells" are cells produced by recovering pluripotent stem cells present in early development which have the ability to differentiate into all tissue cells and making them into a strain that can be cultured in vitro. The ES cells are effectively capable of unlimited growth while retaining the ability to differentiate into all cells that make up an individual in the same way as the pluripotent stem cells of an early embryo.

Specifically, the first ES cells were mouse cells described in 1981 (Martin, Proc. Natl. Acad. Sci. USA 78: pp. 7634-7638, 1981; Evans & Kaufman, Nature 292: pp. 154-156, 1981). These are derived for example from the internal cell mass of a 3.5-day-old embryo. ES cells are pluripotent, capable of producing all tissues and cell types. This is well supported by the fact that when injected into another blastocyst, ES cells can participate in the development of all tissues including the reproductive system, and chimera animals can be obtained in this way. A unique property of ES cells is that they are maintained in a pluripotent stage in the presence of leukemia inhibitory factor (LIF), and are capable of proliferating. At present, this is commonly used for genetic modification of ES cells. Transgenic animals have since been obtained by injecting ES cells treated in this way into a blastocyst. ES cells are also used in studying differentiation in vitro. This method allows research into the development of early tissue under controlled conditions in vitro as well as experimental treatments.

Pluripotent embryonic stem cells have been isolated from a wide variety of species including rats (Iannaconns et al., Dev. Biol. 163: pp. 288-292, 1994), hamsters (Doetschman et al., Dev. Biol. 127: pp. 224-227, 1988), birds, fish, pigs (Wheeler, Reprod. Fertil. Dev. 6: pp. 563-568, 1994), cows (First et al., Reprod. Fertil. Dev. 6: pp. 553-562), and primates (Thompson et al., Proc. Natl. Acad. Sci. USA 92: pp. 7844-7848, 1995). Several research teams have succeeded in isolating ES cells and ES cell-like stem cells from embryonic human tissue (Thompson et al., Science 282: 1145-1147, 1988; Shamblott et al., Proc. Natl. Acad. Sci USA 95: 13726-13731, 1998; Reubinoff, B. E. et al., Nature Biotech 18, pp. 399-404, 2000). These ES cell lines were established by culturing ICMs isolated from blastocysts on feeder cells. Other recent research has shown that embryos and embryonic cells can be obtained by implanting nuclei derived from embryos and mature mammalian cells into denucleated follicular ovarian cells (Campbell et al., Nature 380: pp. 64-66, 1996).

An ES cell line established in any way can be used in the method of the present invention. Alternatively, when ES cells prepared by the method of the present invention are administered to an individual, a method of establishing an ES cell line from a cloned embryo prepared using the somatic cells of an individual is effective for preventing immune rejection reactions. Using this method it is possible to establish ES cells having the same genetic essence as the individual.

In the preparation of somatic cell clones, a phenomenon called "initialization" also occurs in which the nucleus of a somatic cell introduced into an ovum converts to the same state as the nucleus of a fertilized egg. It has been reported that ES cells also have this activity, which is similar to the activity of an egg cell (Tada, M. et al., Cur. Biol. 11: pp. 1153-1158, 2001). That is, it is expected that by fusing the somatic cell of an individual with an ES cell the somatic cell can be converted to a cell similar to an ES cell. Since ES cells can be genetically manipulated in vitro, it is hoped that if this could be applied to ES cells in which factors such as the MHC gene group which are involved in immune rejection have been manipulated in advance, rejection reactions could be avoided without the use of techniques such as somatic cell cloned embryo preparation.

In the present invention, "ES cells" are preferably human ES cells. At present, established human ES cell lines can be obtained from the following institutions for example.

Institute for Frontier Medical Sciences, Kyoto University (Japan)

BresaGen, Inc. (Athen, Ga.)

CyThere, Inc. (San Diego, Calif., USA)

ES Cell International (Melbourne, Australia)

Geron Corporation (California, USA)

Goeteborg University (Sweden)

Karolinska Institute (Sweden)

Maria Biotech Co., Ltd., Maria Infertility Hospital Medical Institute (Seoul, Korea)

MizMedi Hospital, Seoul National University (Seoul, Korea)

National Centre for Biological Sciences, Tata Institute of Fundamental Research (India)

Pochon CHA University (Seoul, Korea)

Reliance Life Sciences (Mumbai, India)

Technion University (Haifa, Israel)

University of California (USA)

Wisconsin Alumni Research Foundation (WARF) (USA)

In the method of the present invention, the ES cells used are preferably in a "differentiating" state. That is, the method of the present invention is characterized by electric pulse treatment of ES cells, but neural cells are not produced simply by electric pulse treatment. The present inventors have shown that the process from ES cells to formation of finally differentiated neural cells can be divided into the following three stages: first, a stage of "de"-undifferentiating or destabilizing the undifferentiated state of the stem cells, second, a stage of regulating the direction of cell fate, and three, a stage in which the fated cells achieved their final differentiated state. In the method of preparing neural cells of the present invention, electric pulse treatment is thought to work only at the second stage.

Consequently, a differentiation-inducing treatment to move the ES cells towards a differentiating state is required either before or simultaneous with electric pulse treatment. When ES cells are cultured to high densities without the addition of a differentiation-inhibiting factor such as LIF (leukemia inhibitory factor) or are made to form a cell mass by float culture with adhesion to the culture dish prevented, they naturally differentiate into a variety of cells. In particular, a cell mass formed by float culture is called an embryoid body (EB) and is the most widely used for causing ES cells to differentiate in vitro. An embryoid body has a ball-like structure consisting of two cell layers, with the inner layer corresponding to the proximal endoderm and the outer layer to the embryonic ectoderm. These two layers are separated by a basement membrane. Within the embryoid body a mesoderm is induced, and muscle cells, blood vessel cells and even primitive vasoganglia develop. When the embryoid body is made to adhere to a culture dish and cultured still further, it differentiates into a variety of kinds of cells.

Methods of inducing ES cells to differentiate in vitro include not only the formation of an embryoid body by float culture but also methods involving secondary culture of ES cells on an extracellular matrix or a supporting layer of cells called stroma cells. Stroma cells are mesenchymal cells that support various kinds of differentiation and proliferation. Cells lines established from bone marrow, neonatal cranial bones and the like are often used in culture. In some cases they themselves are capable of differentiating into fat cells and the like. Because types of cell lineages which tend to be induced for differentiation from ES cells differ depending on the type of stroma cell line or extracellular matrix, this method is suited to selective induction of differentiation into specific cell lineages.

Alternatively, the "differentiating" ES cells of the present invention can be prepared through the use of a differentiation-inducing factor such as retinoic acid or the like.

Consequently, in the present invention "differentiating ES cells" are preferably ES cells differentiation of which has been induced by float culture, stroma cells, extracellular matrix or a differentiation-inducing factor. An embryoid body (EB) formed by float culture is used by preference.

(2) Electric Pulse Treatment

The present invention is based on the finding that when ES cells that have begun to differentiate are treated with an electric pulse, they acquire a strong tendency to move towards differentiation into neuron cells.

The strength of the electric pulse is determined by a combination of the three factors of electric potential, frequency and number of pulses. A person skilled in the art can adjust the strength of the electric pulse appropriately according to such conditions as the type of ES cells used, the type of medium, the type of electrodes and the like. Although this is not a limitation, in a preferred mode of the present invention the electric pulse is applied at a power level of 0.01 W to 10 W or preferably 0.05 W to 6 W (for example, 5 V, 0.01 A to 10 V, 0.6 A). About 5 W is still more desirable. The electric stimulus is applied about three to 10 times about every 900 to 970 ms (preferably 950 ms) for about 30 ms to 100 ms (preferably 50 ms).

The wattage of the electric pulse is important in the present invention, and a relatively high potential, such as 30 V (6 W at 30 V, 0.2 A), is acceptable as long as the current is low. The potential is preferably about 5 V to 30 V or more preferably about 5 V to 10 V. The potential for the electric pulse treatment of the method of the present invention is preferably significantly lower than the potential used for electroporation (generally about 80 V to 2000 V). Consequently, unlike in electroporation it is not strong enough to form holes in the cell membrane, and the cell differentiation-regulating effect of the electric pulse is not attributed to an outflow or inflow of ions due to membrane hole formation (Example 1 (3)).

Electrical pulse treatment can be applied using known methods and equipment. For example, an electroporation (such as Tokiwa Science CUY21E) or micro-electrode (such as Nepa Gene CUY459G20) apparatus can be used. ES cells that have been treated with electric pulse can be maintained on a plate in a suitable medium such as DMEM, alpha-MEM or other synthetic medium containing a nutrient such as fetal bovine serum (FBS, Gibco).

Neural Cells

The present invention also provides neural cells obtained by the method of the present invention. As described in Example 1(3) and the like below in these specifications, the neural cells of the present invention test positive for the TuJ1 antibody, which is a neural cell marker. However, tyrosine-hydroxylase, GAD65, Islet1, Pax6, Pax7, MNR2, Nkx 2.2 and the like, which are markers for final differentiation of specific neural cell types, were not detected in an ex vivo system. This suggests that neural cells obtained by electric pulse treatment could not achieve final differentiation in an ex vivo culture system.

That is, in the present invention it has been shown clearly that differentiating ES cells move towards selective differentiation into neural cells when subjected to electric pulse treatment. The inventors have shown that the process from ES cells to formation of finally differentiated neural cells can be divided into the following three stages: first, a stage of "de"- undifferentiating or destabilizing the undifferentiated state of the stem cells, second, a stage of regulating the direction of cell fate, and three, a stage in which the fated cells achieved their final differentiated state. In the method of preparing neural cells of the present invention, electric pulse treatment is thought to work only at the second stage.

For example, neural stem cell-like cells prepared in the present invention exhibited ex vivo insensitivity to growth factors such as Sonic Hedgehog, BMP, FGF and Noggin, which are thought to affect cell fate determination (Example 1(5)). On the other hand, it was shown that they have the ability to assume a variety of finally differentiated neuron states in an in vivo environment (Examples 2 and 3). This means that the neural cells of the present invention are "plastic for final differentiation," requiring a separate step (third step) to follow the expected neural fate for final differentiation. They do not express any of the specific neuron markers that indicate neuron type, and have the ability to follow any neuron fate in vivo. In culture, meanwhile, they continue to not express such markers even when exposed to growth factors.

Consequently, the neural cells of the present invention are preferably non-reactive to exposure to growth factors in vitro and ex vivo. In vivo, they are preferably capable of final differentiation into specific neural cells. Consequently, the neural cells of the present invention are preferably neural stem cell-like nervous system cells which are capable of final differentiation into specific types of neural cells such as neurons, glia, astrocytes, oligodendrites and the like, and of constructing nerve tissue.

In Example 3 of these specifications, an electric pulse-treated EB was deliberately injected using a spinal cord damaged mouse as the recipient in order to determine whether or not an electric pulse-treated EB had the ability to form adult nerve tissue in vivo. As a result, it was found that the electric pulse-treated embryoid body of the present invention contributed to spinal cord nerve tissue in the mouse, resulting in improved motor dysfunction (FIG. 9). The exact mechanism by which the neural cells of the present invention form adult nerve tissue in vivo is unknown, but since it is known that glia cells can develop from adult neuron stem cells in response to spinal cord damage (Non-Patent Publication 14), it is possible that the damage provided the environmental signal needed to direct the final differentiation of the injected cells in the appropriate direction. It is also known that environmental changes in response to injury can affect the presence of growth factors and cytokines capable of regulating proliferation and differentiation of neuron stem cells (Non-Patent Publication 6). In contrast, the control non-treated embryoid body only formed an accumulated cell mass at the transplantation site and did not differentiate appropriately.

Thus, the neural cells of the present invention are preferably non-responsive to exposure to growth factors in vitro and ex vivo, maintaining a neural stem cell-like state, but have the ability to follow any cell fate in vivo.

Pharmaceutical Composition

Unlike conventional methods using growth factors, the method of preparing embryonic stem cells of the present invention produces young or "plastic" neural lineage cells or in other words neural stem cell-like neural cells which are quite versatile, capable of adapting their behavior to environmental conditions and differentiating into cells suited to the site to which they have been transplanted. Consequently, the neural cells of the present invention can be applied therapeutically.

In fact, as described in Example 3 of these specifications, an electric pulse-treated EB was deliberately injected using a spinal cord damaged mouse as the receptor in order to determine whether or not an electric pulse-treated EB had the ability to form adult nerve tissue in vivo. As a result, it was found that the electric pulse-treated embryoid body of the present invention contributed to spinal cord nerve tissue in the mouse, resulting in improved motor dysfunction.

Most previously reported therapeutic applications have not required the formation of appropriate neuron circuits, as in the case of Parkinson's disease therapy (Non-Patent Publications 15-16). The neural cells of the present invention are capable of helping motor dysfunction, suggesting that they can reconstruct function structures. This is interesting in connection with the fact that electric pulse is used to treat a number of psychiatric conditions such as schizophrenia and depression (Non-Patent Publications 17). It has been shown in the present invention that ES cells that have started to differentiate acquire a strong tendency to move towards differentiation into neuron cells when subjected to an electric pulse, suggesting that neuron cell regeneration and neural circuit reconstruction may occur when electric pulse is used to treat psychiatric patients.

Consequently, the present invention provides a pharmaceutical composition for preventing or diagnosing neural-related diseases or damage comprising the neural cells of the present invention.

In these specifications, "neural-related diseases or damage" includes any diseases or damage stemming from congenital or acquired degeneration, damage or the like of the nerves. Known neural-related diseases include for example spinal cord damage, head injury (cranial fracture, intracranial hematoma, brain damage, etc.), circulatory disorders (cerebral ischemia, brain lesions due to hypoxia, intracranial bleeding, etc.), infections (viral infections, prion diseases, bacterial infections, fungal infections, parasitic infections, etc.), demyelination diseases (multiple sclerosis, acute diffuse encephalomyelitis, etc.), degenerative diseases (neurodegenerative diseases whose main symptom is dementia, neurodegenerative diseases whose main symptom is motor and posture control impairment, neurodegenerative diseases whose main symptom is ataxia, ataxia of autosomal-dominant inheritance, neurodegenerative diseases whose main symptom is disorder of the motor nervous system, etc.), poisoning and radiation damage (neural disorders caused by poisoning, radiation damage, etc.), neural damage accompanying nutritional disorders (thiamine deficiency, pellagra, subacute combined degeneration of the spinal cord, etc.), neuropathy accompanying congenital metabolic abnormalities (neuropathy accompanying mitochondrial DNA abnormalities, neuropathy accompanying lysosomal enzyme abnormalities, neuropathy accompanying peroxisome abnormalities, neuropathy accompanying leukodystrophy and amino acid metabolism abnormalities, diseases caused by trace metal metabolism abnormalities, etc.), neuropathy accompanying acquired metabolic abnormalities (hepatocerebral disease, Reye's syndrome, hypoglycemic encephalopathy, central pontine myelinolysis, dialysis encephalopathy, etc.), intracranial tumors (glioma, tumors stemming from neural cells, tumors derived from undifferentiated cells, meningeal tumors, peripheral nerve tumors, pineal tumors, primary lymphomas, etc.), deformities (aplasia of the neural tube due to inadequate closure of the neural groove, developmental abnormalities following neural tube formation, deformation due to abnormalities of embryo cell differentiation and movement, neural disorders caused by perinatal abnormalities, deformation of the spinal cord and around the foramen magnum, phakomatosis, etc.), peripheral nerve lesions and the like.

Neurons, glia and other neural cells are known to be involved in spinal cord damage, cerebral ischemia including cerebral infarction, circulatory disorders including brain lesions due to hypoxia and the like. Consequently, the pharmaceutical composition of the present invention can be used preferably to prevent or diagnose neural-related diseases or damage selected from spinal cord damage and cerebral infarction. More preferably it can be used for spinal cord damage.

Most preferably, the composition of the present invention can prevent or diagnose neural-related diseases or damage when transplanted by injection or the like into the spinal cord or neural tubes of a living organism. Administration can be by a known method. The amount of neural cells needed for transplantation differs depending on such factors as the species, age and sex of the organism, the disease and severity and the like. In general, a total of about 1 ml to 10 ml of neural cells with a concentration of about $10^7$/ml is thought to be necessary.

The organism to which the composition of the present invention is administered is not particularly limited but is preferably a higher organism for which ES cells have been established. Examples include rats, hamsters, birds, fish, pigs, cows and humans and other primates, for which ES cells have been established as described above.

BRIEF DESCRIPTION OF THE DRAWINGS

FIGS. 1a and 1b show the rates of appearance of colonies containing neuron identity (a) and muscle marker-expressing (b) cells. FIGS. 1c and 1d show the numbers of cells positive for a neuron marker (c) and a muscle marker (d) in an individual colony.

FIGS. 2a through 2c show control non-pulse-treated embryoid bodies (EBs). A few colonies contained TuJ1-positive cells (2c), but most colonies did not contain TuJ1-positive cells (2a). In FIG. 2a, the nuclear stain of the embryoid body indicates cell density. FIGS. 2d through 2h show electric pulse-treated EBs. Anti-TuJ1 immune stains of EBs treated with 5 V (2d), 10 V (2e) and 20 V (2f) are shown. FIG. 2g is a higher magnification of the TuJ1 immune stain of the EB treated with 10 V. FIG. 2h shows an anti-a-actin stain of an EB treated with 10 V. In FIG. 2i, nuclear staining indicates the presence of cells. In FIG. 2j, an anti-Tuj1 stain of the embryoid body treated with 10 V which was shown in FIG. 2h indicates no signs of neuron differentiation in the ES cells. Nuclear staining was done with propidium iodide.

The reduced scale lines indicate 1 mm (a-c), 100 mm (d-f, h), 500 mm (g) and 200 mm (i, j).

Figure 3:
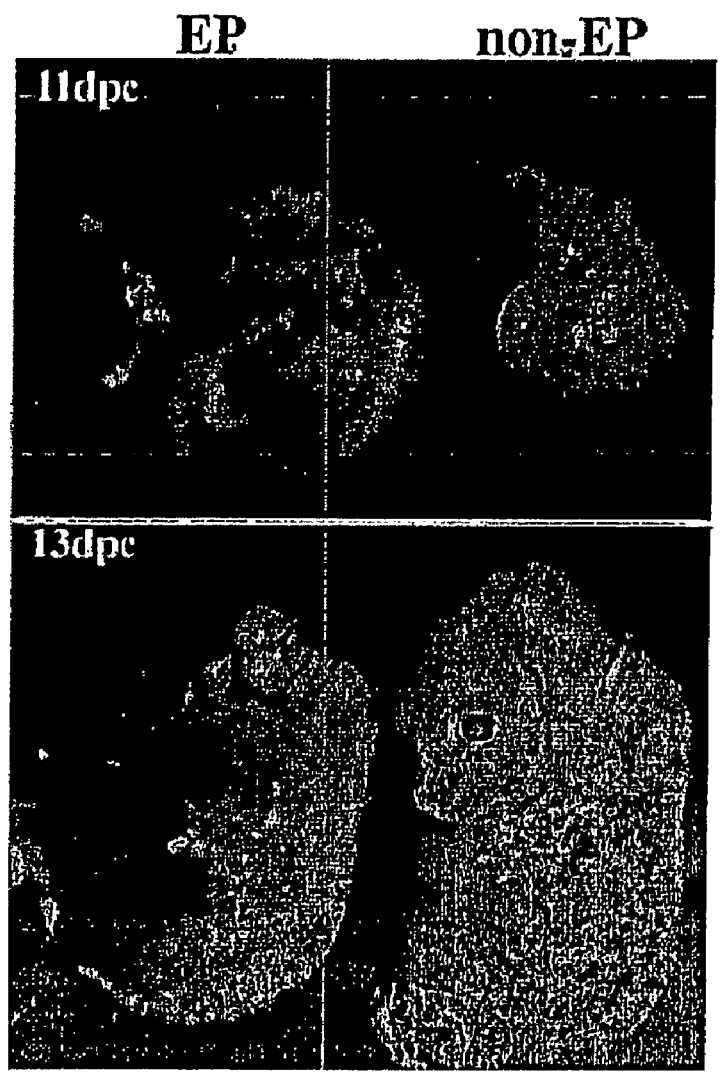

FIG. 3 shows images of whole tissue specimens of receptor embryos for Venus-positive embryonic stem cells. 11 dpc embryos are shown in the top panel and 13 dpc embryos in the bottom panel. In both panels, the embryo on the left received electric pulse-treated embryonic stem cells at the blastocyst stage, while that on the right is a receptor for untreated embryonic stem cells. In both cases the embryos on the left exhibit a clear tendency toward dorsal (neural) fluorescence distribution, while the embryos on the right exhibit a rather ubiquitous distribution of fluorescent cells.

Figure 4:
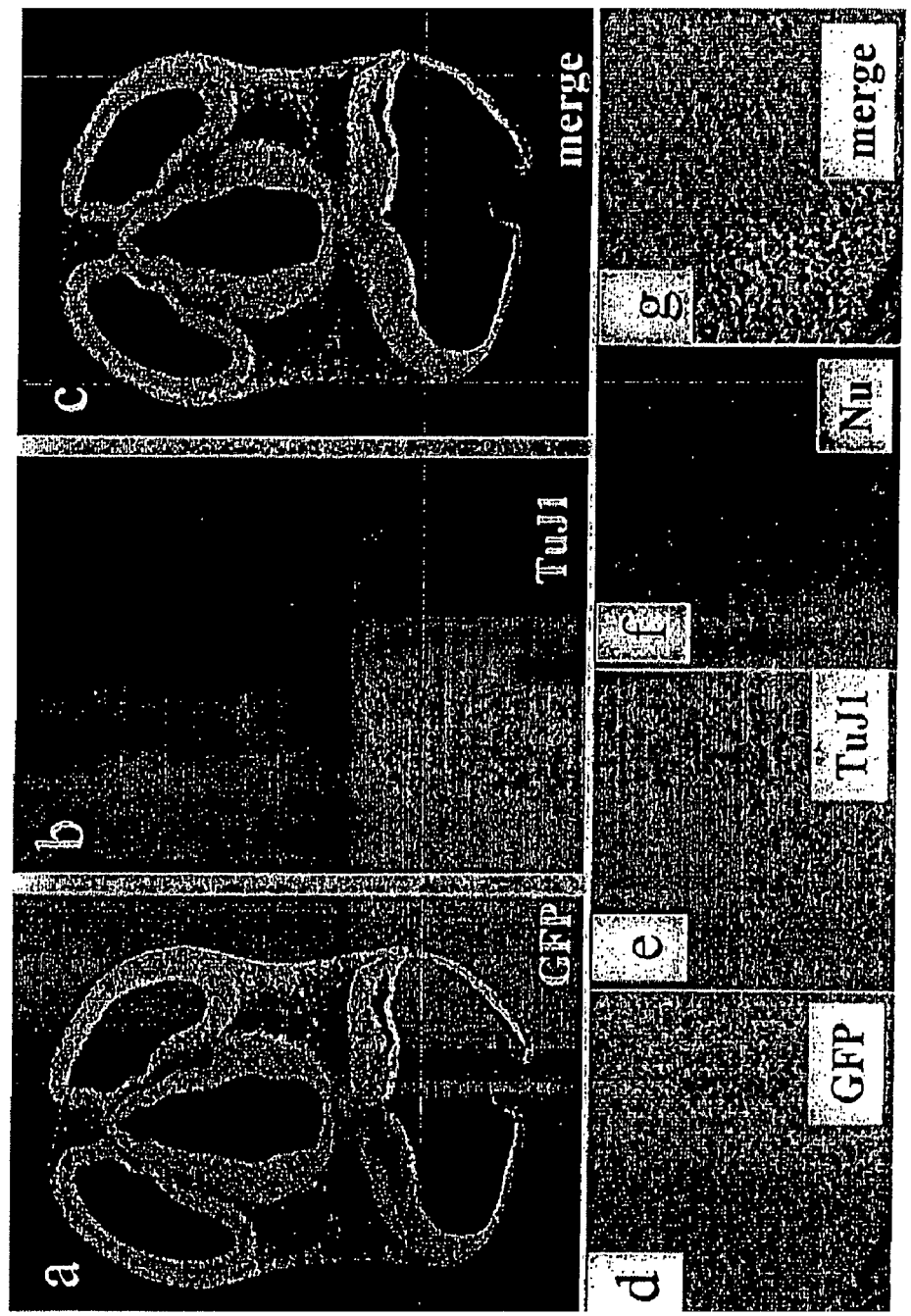

FIG. 4 shows the distribution of electrically-treated embryonic stem cells in a mouse embryo.

An 11 dpc embryo was cut into sections to examine the cell types of fluorescent embryonic stem cells in the central nervous system. Intake of embryonic stem cells into brain (a-c) and spinal cord (d-g) neurons was seen. Green fluorescence indicates anti-GFP-positive cells expressing Venus (a, c, d, g), while red indicates TuJ1-positive cells for identifying differentiated neurons (b, e, g), and blue is a nuclear stain with Topro3 showing the presence of cells (f, g). The reduced scale lines indicate 500 µm (a-c) and 250 µm (d-g).

Figure 5:
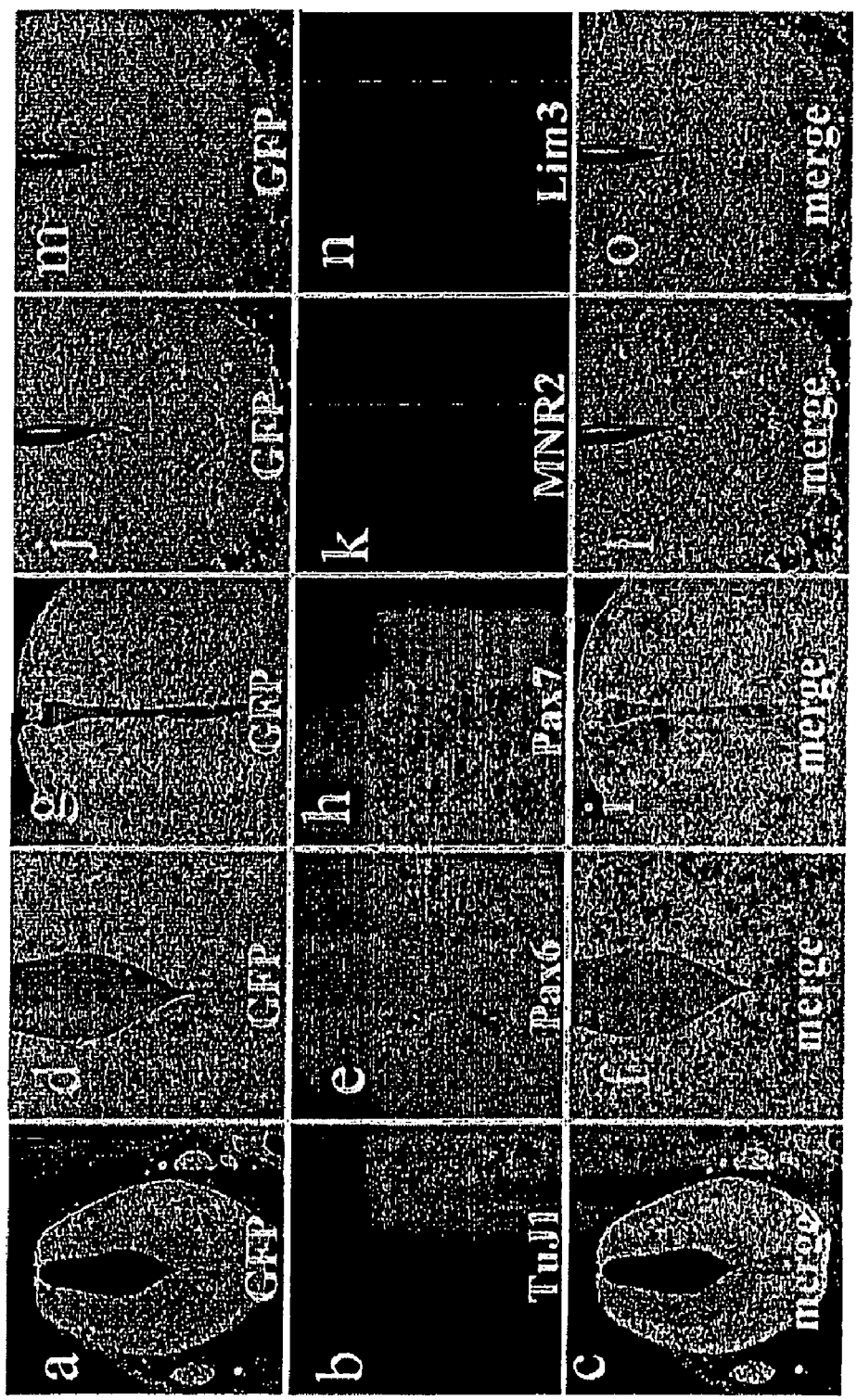

FIG. 5 shows the distribution of electrically-treated embryonic stem cells in a mouse embryo.

An 11 dpc embryo was cut into sections to examine the cell types of fluorescent embryonic stem cells in the central nervous system. Intake of ES cells into the spinal cord (a-o) neurons was seen. Green fluorescence indicates anti-GFP-positive cells expressing Venus (a, c), while red shows TuJ1-positive cells for identifying differentiated neurons (b, c), and blue is a nuclear stain with Topro3 showing the presence of cells (c).

FIGS. 5d through 5o are panels from a detailed analysis of contributing ES cell specificity, and show the differentiation of ES cells into a variety of types of neurons, including motor neurons, interneurons and precursors thereof. The green signal likewise indicates GFP-positive cells. The red signal indicates Pax6 (e, f), Pax7 (h, i), MNR2 (k, 1) and Lim3 (n, o).

The reduced scale lines indicate 100 µm (a-c) and 100 µm (d-o).

Figure 6:
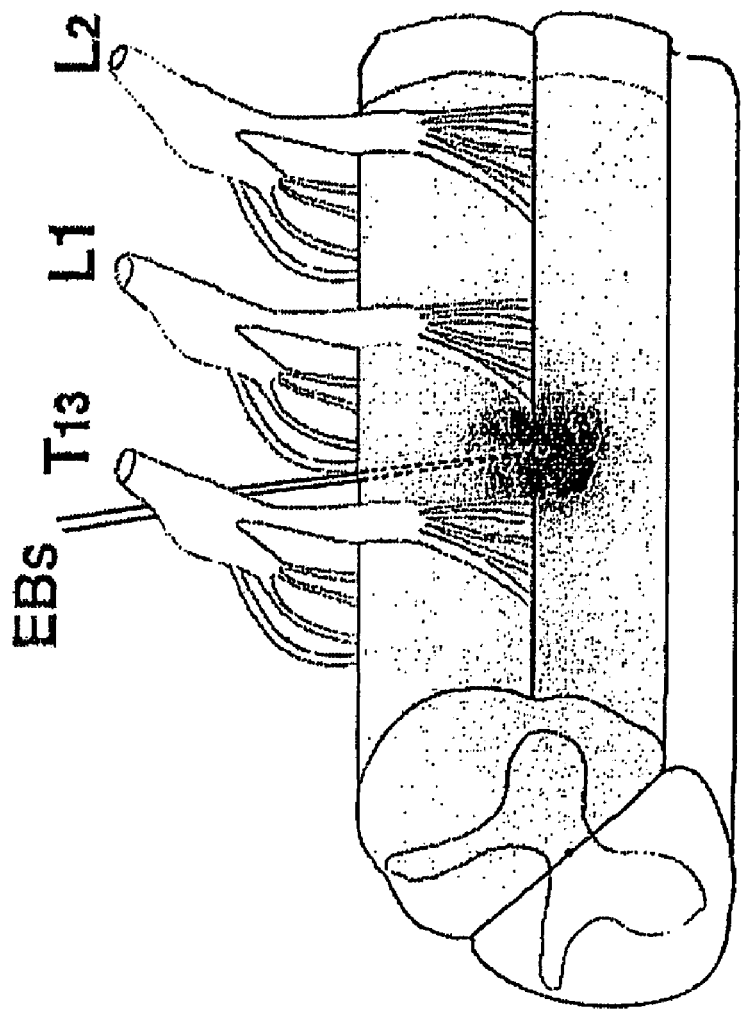

FIG. 6 shows the scheme of an impact injury protocol. After separation of the vertebrae, the spinal cord corresponding to T13-12 was subjected to a weight-drop impact injury. 10 days after the injury treated and untreated ES cells were injected.

Figure 7:
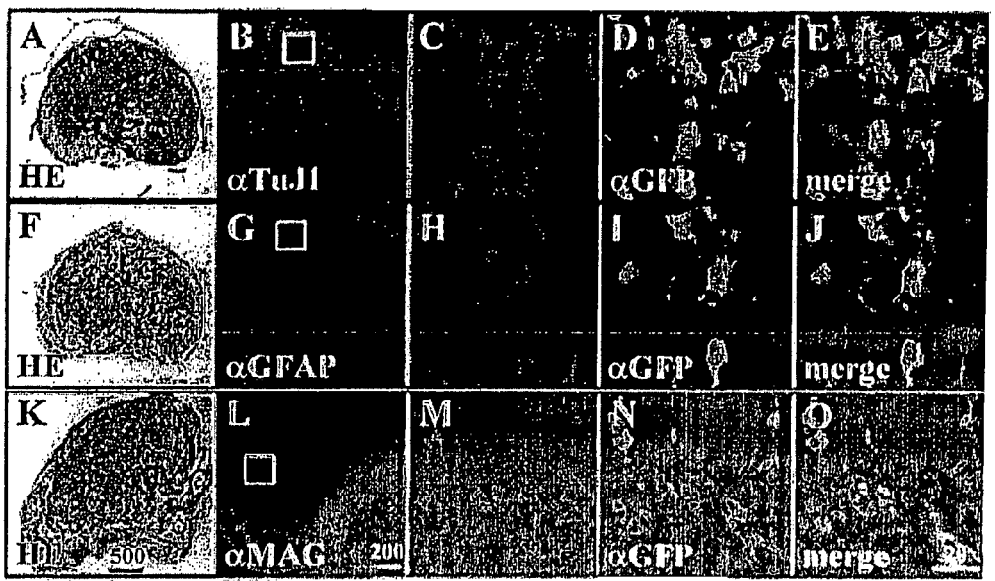

FIG. 7 shows the contribution of ES cells to adult injured spinal cord. The sections show differentiation of ES cells into TuJ1-positive neurons (a-e), GFAP-positive glial cells (f-j), and MAG-positive oligodendrocytes (k-o).

FIGS. 7a, f and k are hematoxylin-eosin stains. The green signal in all panels is GFP, while the red signal indicates antibody staining for TuJ1 (b, c, e), GFAP (g, h, j) and MAG (l, m, o).

The reduced scale lines indicate 500 mm (a, f, k), 200 mm (b, g, l) and 20 mm (c-e, h-j, m-o). The white rectangles in b, g, and l indicate the regions shown at higher magnification in c-e, h-j and m-o, respectively.

Figure 8:
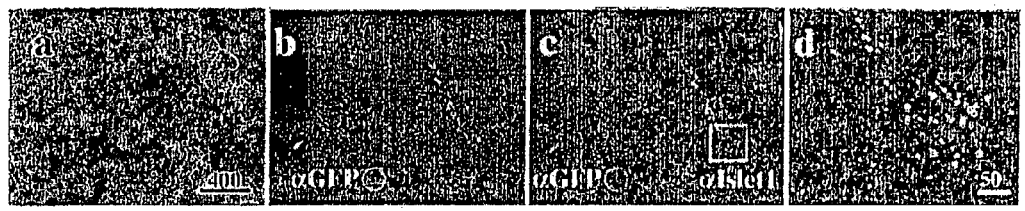

FIG. 8 shows the contribution of ES cells to adult injured spinal cord, and particularly ES-derived cells that have differentiated into Islet-1-positive motor neurons. The green signal in all panels is GFP, while the red signal indicates antibody staining for Islet-1 (a, c, d). The reduced scale lines indicate 400 mm (a-c) and 50 mm (d). The white rectangle in c indicates the region shown at higher magnification in d.

Figure 9:
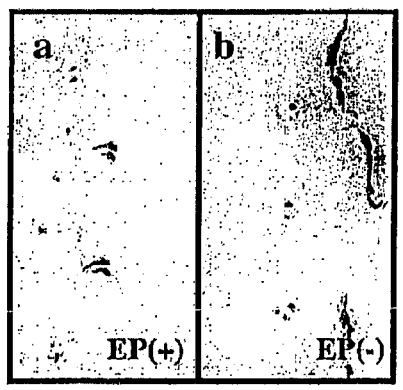

FIG. 9 shows the contribution of embryonic stem cells to adult injured spinal cord, and particularly the recovery effects of electrically-treated embryonic stem cells in motor function injury in a mouse. As shown by the mouse footprints in FIG. 9, the mouse that received electrically-treated embryonic stem cells exhibited normal motor activity (a), while the control mouse that was injected with an untreated embryoid body exhibited no signs of recovery (b).

Figure 10:
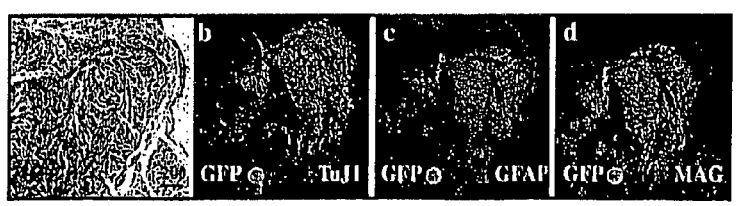

FIG. 10 shows that a non-pulse-treated embryoid body formed a cell mass without dispersing to contribute to spinal cord tissue. 10a is a hematoxylin-eosin stain. The green signal is GFP in all panels, while the red signal indicates antibody staining for TuJ1 (b), GFAP (c) and MAG (d). The reduced scale line indicates 200 mm (a-d).

EXAMPLES

The present invention is explained in detail below using examples, but these do not in any way limit the technical scope of the present invention. A person skilled in the art could easily add modifications and changes to the present invention based on what is described in these specifications, and these are included in the technical scope of the present invention.

Methods

Histology

Cultured cells or sections were treated using the following antibodies for immunohistochemical purposes:

anti-TuJ1 mouse monoclonal antibodies (mAb) (1:500; BAbCO);

anti-GFAP rabbit polyclonal antibodies (pAb) (1:5; DAKO);

anti-MAG rabbit polyclonal antibodies (1:500; the late Prof. Yoshihiro Matsuda);

anti-GAD65 polyclonal antibodies (1:200; Chemicon);
anti-TH mAb (1:500; Boehringer);
anti-Nestin mAb (1:500);
anti-Islet1 mAb (1:400; DSHB);
anti-Pax6 mAb (1:200; DSHB);
anti-Pax7 mAb (1:400; DSHB);
anti-MNR2 mAb (1:400; DSHB) and
anti-Nkx2.2 mAb (1:400; DSHB).

Example 1

Cell Fate Determination of Electric Pulse-Treated Cells in Culture (1) The effects of intracellular and extracellular ion balance on differentiation fate were tested by application of electricity. An EB was first prepared by known methods as described below, and an electric pulse was applied to the EB with electrodes.

First, embryonic stem cells expressing Venus were isolated by electroporation of R1 ES cells (obtained from Prof. Andreas Nagy at Mount Sinai Hospital (Toronto, Canada)) expressing the Venus protein (obtained from Prof. Atsushi Miyawaki of the Institute of Physical and Chemical Research Brain Science Institute) induced by the CAGGS promoter (obtained from Prof. Junichi Miyazaki of Osaka University) (Non-Patent Publications 9 and 18). An embryoid body was prepared by culturing ES cells using DMEM comprising 10% FCS in an adhesion-proof bacterial Petri dish (Nunc).

"Venus" is a variant of EYFP, which is itself a variant form of GFP (green fluorescent protein), and is widely used as a fluorescent label marker. EYFP is a known fluorescent protein, and its amino acid sequence is deposited at NCBI as record number AAF65455. Venus has modifications to the following 5 amino acid residues of the EYFP sequence, and exhibits extremely strong fluorescent activity: F47L/F65L/M154T/V164A/S176G.

An electric pulse was applied using an electroporator (CUY21E, Tokiwa Science) in a 4 mm gap cuvette under different potential conditions (0 V, 5 V, 10 V and 20 V). Specifically, a 5-6 W electric stimulus was applied 5 times for 50 ms at 950 ms intervals. The electric pulse-treated embryoid body was maintained in DMEM containing 10% fetal bovine serum (FBS, Gibco) on a poly-D-lysine coated plate (BD). 10 days later, the cells were fixed for purposes of immunohistochemical observation.

Figure 1:
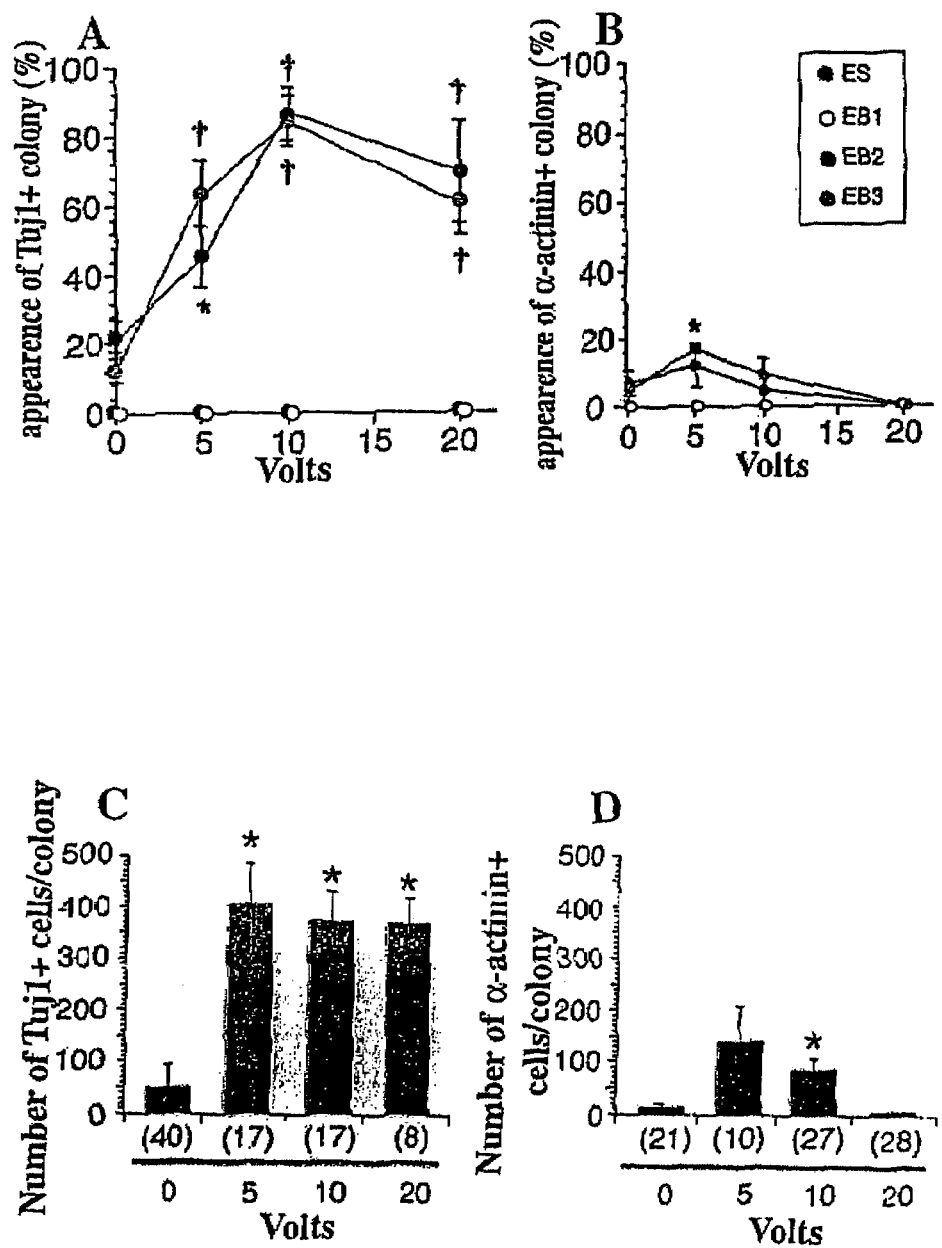
FIG. 1 shows the effects of an electric pulse on ES cells in the process of differentiation in a culture system.
Figure 2:
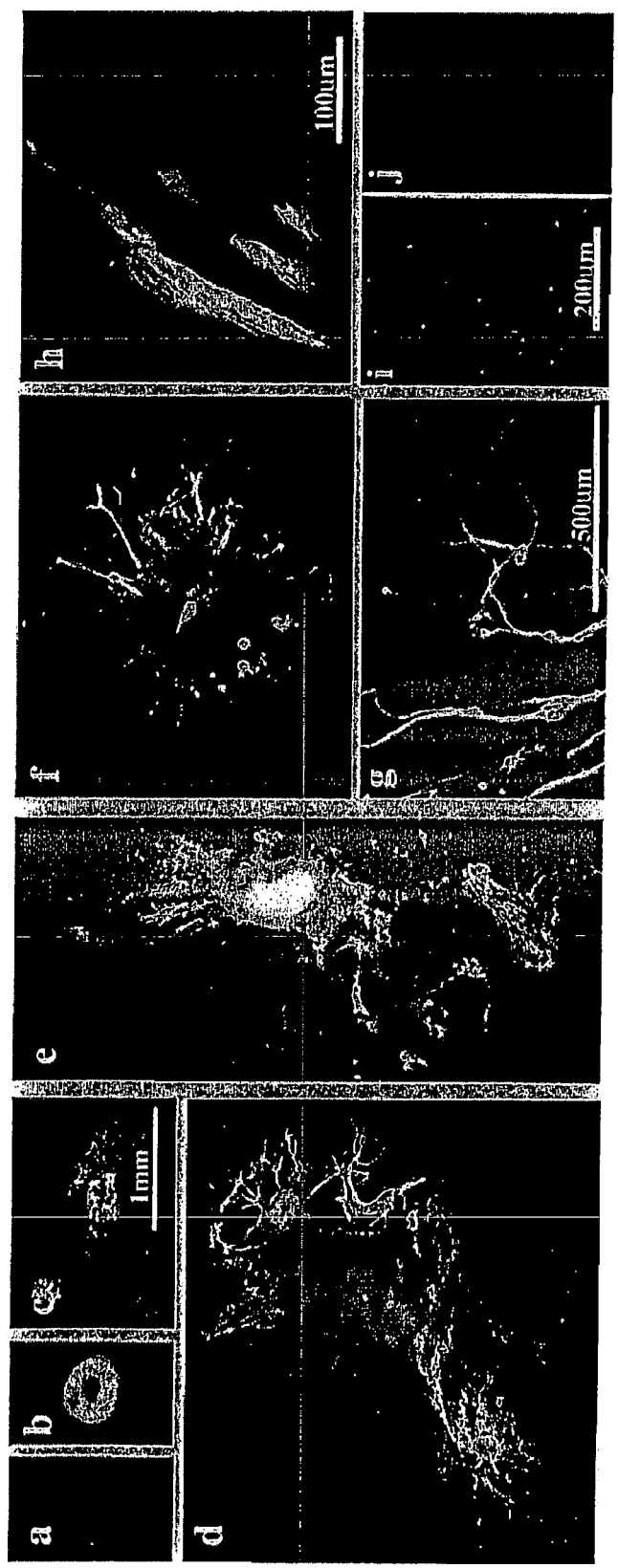
FIG. 2 shows the effect of an electric pulse on ES cells in the process of differentiation in a culture system.

After 10 days of culture on a poly-D-lysine coated plate, the cells were fixed to test their fates by differentiation. The original R1 embryonic stem cells that had received no electric pulse exhibited no specific tendencies towards cell fate (FIG. 2a) as shown by the differentiation markers (mainly muscle and neuron) used. Surprisingly, however, the cells of the embryoid bodies in the pulse experiments exhibited strong neuronal differentiation in comparison to those of embryoid bodies that were not pulse treated (FIGS. 1 and 2). In the pulse treated group, almost all colonies treated with 10 V contained neuron cells. In the non-pulse-treated control group, less than 10% of the colonies contained TuJ1-positive cells (that is cells fated to become neurons) (FIG. 1). In all cases, a single colony containing TuJ1-positive cells contains about 500 cells for neuron differentiation, but neuron fate appeared in the 10 V treated embryoid bodies about 10 times more than in the 0 V treated bodies (FIGS. 1a, c). Within the colonies with 10 V treatment it was estimated that about half the cells would follow a neural fate during the early period, but there was no accurate means of calculating the ratio of cells which followed a neuron fate in a single colony. Neuron fated cells (which are expected to stop proliferating in the early stage of differentiation) can be cultured together with non-specific proliferating cells for 10 days within the same colony so that the minority proliferating group becomes the majority.

At a potential of 5 V, about 40% of the colonies contained TuJ1-positive cells, but the total appearance of neuron cells seemed to be the same as in the 10 V pulse treated embryoid bodies (FIGS. 1a-d). This indicates that neuron cell appearance in each colony was twice as high at 5 V as at 10 V. A 20 V pulse seems to produce some toxicity in the cells. These cells express TuJ1, but the cell bodies exhibit strange morphology with thick dendrites.

Interestingly, although the muscle-fated cells exhibited a slight tendency to increase when treated with 5V, there was no significant increase in appearance (FIGS. 1b, d). This indicates that the pulse effect can be clearly distinguished during the differentiation fate period, with cell differentiation being strongly adjusted in the direction of neurons.

(2) The electric pulse itself is not a factor which initiates differentiation, but rather a factor which regulates the direction of cells which have started to differentiate. It has the effect of regulating cell fate only when applied to cells that have already started the differentiation process. However, it is noteworthy that differentiation markers such as tyrosine-hydroxylase, GAD65, Islet1, Pax6, Pax7, MNR2 and Nkx2.2 (data not shown) which may be final differentiation markers for specific neuron cell types, were not detected in the ex vivo system. These observations suggest that the TuJ1-positive cells that appeared were not able to achieve final differentiation in this culture system.

(3) To obtain information about the mechanism of regulation of fate determination, we initially tested pore formation in cell membranes by electric pulse using a trypan blue stain. An electric pulse was applied to the cells in a reagent containing trypan blue. No blue stain was observed at 5 or 10 V, which were the conditions used in the subsequent differentiation tests, but cells became stained at 20 V (data not shown). These tests indicate that unlike in the case of electroporation (data not shown), the regulatory effect of electric pulse is not due to ion outflow or inflow due to membrane fractures, since the pulse is too weak to create pores in the cell membrane.

(4) Cell dissociation can be another important factor in observations of colony form. While colonies containing no neurons had a distinct round shape, colonies containing TuJ1-positive cells were more dispersed. However, since embryoid bodies detached without an electric pulse did not appear different in terms of appearance of neuron differentiation, it was concluded that while detachment is an important factor (data not shown) it is not a key factor.

(5) Corresponding to our observations regarding neuron precursor cell formation from differentiating ES cells, application of growth factors (for example, the presence of fibroblast growth factor 2 (FGF2) followed by elimination of FGF2) is considered necessary for final differentiation of neuron precursor cells (Non-Patent Publication 6). As mentioned before, the differentiated neuron cells in this example do not express specific markers of neuron tissue cell types such as motor neurons or dopaminergic neurons. These results create two possibilities. First, either these neuron cells have a neuron identity outside our marker repertory, or they are instead young, adaptable neuron precursor "plastic" cells. Further exposure to various growth factors such as Sonic Hedgehog, BMP, FGF and Noggin, which are normally thought to affect cell fate determination, had no effect on the pulse-treated embryoid bodies. In the differentiated neuron system of this example, the neuron lineage cells did not respond to a single factor as specific final differentiation (data not shown), but these environmental factors are probably essential for final differentiation in vitro and in vivo.

Example 2

Neuron Contribution of Electric Pulse-Treated ES Cells to Embryos (1) In the ex vivo experiment of Example 1, the resulting neuron precursor cells did not appear to have any responsiveness to growth factors. Treated and non-treated ES cells were injected into mouse embryos at various stages to test the biological ability of these cells.

Specifically, 10 V pulse-treated Venus-positive embryoid bodies (EBs) were dissociated for 3 minutes with trypsin-EDTA. The dissociated cells were injected into C57BL/6 blastocysts. The resulting embryos were fixed with 0.05 M phosphoric acid buffer (pH 7.4) containing 4% formaldehyde at E11.5 or E13.5 for immunohistochemical purposes.

12 embryos and 15 embryos were collected from injection into blastocysts of 10 V pulse-treated and untreated control cells, respectively. An ES cell line (Non-Patent Publication 9) with ubiquitous expression of Venus (EYFP derivative) was used to follow cell fates with fluorescence and/or GFP antibodies in these assays.

The original ES cell line, called LCVL10, contributed dramatically to embryoid bodies and neonates. Surprisingly, in 9 embryos which were collected at 11 dpc (days post coitum) and 3 embryos which were collected at 13 dpc the electrically-treated cells exhibited a clear tendency to be incorporated into neural tissue. 5 embryos (4 from 11 dpc and 1 from 13 dpc) were extremely similar to one another, exhibiting mainly contribution of fluorescent cells to the dorsum or in other words the central nervous system (FIG. 3) and secondary distribution to other tissues including the peripheral nervous system (PNS). Two others from 11 dpc exhibited slight contribution to the PNS, while one from 13 dpc exhibited strong contribution to the heart and secondary contribution to the PNS.

When non-pulse-treated embryoid bodies were injected into blastocysts, 10 embryos were collected at 11 dpc and 5 embryos at 13 dpc. In contrast to the treated embryoid bodies, at least half of which exhibited unique contribution to the embryoid bodies, the non-treated embryoid bodies contributed inefficiently to the embryoid bodies. One embryo each from 11 dpc and 13 dpc exhibited ubiquitous contribution not only in the embryoid body but also outside the embryoid body such as in the yolk sac, as is observed with the original ES cell strain (FIG. 3). The other two specimens exhibited strong fluorescence in the yolk sac, without any particularly contribution to the embryoid body.

In these experiments, cells from a pulse treated EB exhibited a stronger tendency than non-pulse-treated cells to contribute to the embryoid body and particularly to the neuron tissue.

(2) To clarify the cell types of the ES-derived injected cells, the collected embryos were stained in sections with the antibodies described in the methods section.

As a result, the GFP-positive ES-derived cells exhibited a clear deflection towards neuron tissue in the cross-section. These cells, which were detected in the CNS, exhibited neuron identity and were simultaneously stained with GFP and antibodies to TuJ1, Islet1, Pax6, Pax7 and MNR2 gene products (Non-Patent Publication 10) (FIGS. 4-5). These results suggest that although reagents for motor neuron differentiation such as Sonic Hedgehog and the like did not induce neurons with clear identity in a culture system, these cells were at least capable of differentiation into suitable functional neurons regardless of neuron specificity.

Consequently, cells produced by these methods clearly have the potential to differentiate into normal neurons in the environment of a living body. In some embryos cell incorporation tended to be rather in the direction of ventral spinal cord including motor neurons and interneurons, but these cells can basically assume all neuron fates across the dorsoventral axis (FIGS. 4-5). These cells also formed forebrain, hindbrain, brain stem and spinal cord regardless of anteroposterior identity (FIGS. 4-5).

Putting all this together, our data suggest that electric pulse-treated embryoid bodies can first return to an initial neuron cell stage. Moreover, they seem to have the plasticity to contribute to any neuron specificity depending on the environment into which they are incorporated, which partially resembles a report (Non-Patent Publication 11) that neural stem cells generate neural cholinergic neurons in response to the transplantation environment.

Example 3

Formation of Adult Neuron Tissue (1) Using adult injured spinal cord as the recipient, electric pulse-treated embryoid bodies were deliberately injected to determine whether electric pulse-treated embryoid bodies have the ability to contribute to neuron tissue (FIG. 6). The present invention offers new potential for recovery from motor dysfunction.

To create vertebral damaged mice, adult 129 SvEv mice were anesthetized with pentobarbital (50 mg/kg, ip.), and the spinal cord at the T13-L2 level was subjected to a weight-drop shock. 10 days later, Venus-positive embryoid bodies were transplanted into the shock injured mice. The embryoid bodies were injected into the damaged spinal cord at the L1 level. 20 days after transplantation, sections were treated for immunohistochemical purposes. All mice were maintained at the RIKEN-BSI animal facility in accordance with laboratory guidelines.

(2) As can be seen from the footprints in FIG. 9, all the injured mice who received the treated embryoid bodies exhibited recovery of motor function, and could walk normally within 20 days (FIG. 9a), while the non-treated controls continue to drag their feet and did not recover (FIG. 9b).

(3) 20 days after transplantation, neuron marker expression was analyzed in the spinal cord that had received transplantation (FIGS. 7-8). Using a number of markers to identify neuron precursors, it was shown that these Venus-expressing cells detected by GFP antibodies may be accompanied by glial fibrillary acidic protein (GFAP)-positive astrocytes, myelin-associated glycoprotein-positive oligodendrocytes and TuJ1-positive neurons (FIGS. 7a-o). Moreover, Islet1, which is known to be a spinal cord motor neuron marker (Non-Patent Publication 12) was also detected in this example (FIGS. 8a-d). Thus, the electric pulse-treated embryoid bodies contributed well to spinal cord tissue.

(4) By contrast, the non-pulse-treated embryoid bodies formed cohesive cell masses at the transplantation sites. These Venus-positive cell masses did not express either TuJ1, GFAP or MAG, and even seemed to be excluded from neuron tissue (FIG. 10). Moreover, phosphorylated histone H3 was not detected in these cell masses, suggesting that the cells had stopped proliferating (data not shown). In most transplantation experiments of neural stem cells and embryonic stem cells, most of these cells differentiated towards glia, and only a very small proportion of cells are reported to have contributed to neuron lineages (Non-Patent Publication 13).

These findings indicate that embryoid bodies acquire the character of neuron precursor cells when exposed to an electric pulse, and that these electric pulse-treated embryoid bodies finally differentiate at least into motor neurons in response to environmental factors supplied at the transplantation site.

Example 4

Nerve Differentiation of ES Cells Using Micro-Electrodes

Embryoid bodies were treated with micro-electrodes (Nepa Gene CUY459G20), and cell fate determination was investigated as in Example 1. Embryoid bodies were prepared by culturing ES cells (obtained from Prof. Andreas Nagy at Mount Sinai Hospital) in DMEM medium containing 10% FCS in a cell adhesion-proof Petri dish. These embryoid bodies were subjected to an electric pulse in DMEM medium containing 10% FCS or in Hank's Balanced Medium. The strength of the electric pulse was 30 V, 0.2 A (6 W). The cells were then cultured DMEM medium containing 10% FCS or in Hank's Balanced Medium in an adhesive dish. Nerve differentiation of the embryoid bodies was observed as a result.

The invention claimed is:

1. A method for increasing the yield of neural precursor cells in vitro or ex vivo, comprising electric pulse treating an embryoid body to obtain said increased yield of neural precursor cells, wherein said electric pulse treatment comprises the application of a potential ranging from 1250 to 5000 V/m, wherein said yield of neural precursor cells is increased in comparison to cells not treated with said electric pulse treatment.

2. The method according to claim 1, wherein the electric pulse treatment is applied at a power level of 0.01 W to 10 W.

3. The method according to claim 1, wherein the electric pulse treatment is applied at a power level of 0.05 W to 6 W.

4. The method according to claim 1 or 2, wherein the differentiating ES cells are an embryoid body formed by float culture.

5. The method according to claim 1 wherein the embryoid body comprises human embryonic stem cells.

6. The method of claim 1, wherein said electric pulse treatment comprises the application of five electric pulses in a five second period.

7. The method of claim 1, further comprising culturing said embryoid body after said electric pulse treatment in DMEM media comprising 10% ECS.

* * * * *